United States Patent
Wang et al.

(10) Patent No.: US 12,012,627 B2
(45) Date of Patent: Jun. 18, 2024

(54) METHOD FOR PRODUCING PSICOSE 3-EPIMERASE BY HIGH-DENSITY FERMENTATION

(71) Applicants: Sanying Wang, Luohe (CN); Linzheng Li, Luohe (CN); Ziheng Jin, Luohe (CN); Yanjun Wen, Luohe (CN)

(72) Inventors: Sanying Wang, Luohe (CN); Linzheng Li, Luohe (CN); Ziheng Jin, Luohe (CN); Yanjun Wen, Luohe (CN)

(73) Assignee: HENAN ZHONGDA HENGYUAN BIOTECHNOLOGY STOCK CO., LTD., Luohe (CN)

( * ) Notice: Subject to any disclaimer, the term of this patent is extended or adjusted under 35 U.S.C. 154(b) by 0 days.

(21) Appl. No.: 18/154,827

(22) Filed: Jan. 15, 2023

(65) Prior Publication Data

US 2023/0304057 A1 Sep. 28, 2023

(30) Foreign Application Priority Data

Mar. 22, 2022 (CN) .......................... 202210288790.2

(51) Int. Cl.
| | | |
|---|---|---|
| *C12P 19/24* | (2006.01) | |
| *C12N 1/20* | (2006.01) | |
| *C12N 9/90* | (2006.01) | |
| *C12N 15/52* | (2006.01) | |
| *C12N 15/75* | (2006.01) | |
| *C12R 1/125* | (2006.01) | |

(52) U.S. Cl.
CPC .............. *C12P 19/24* (2013.01); *C12N 1/205* (2021.05); *C12N 9/90* (2013.01); *C12N 15/52* (2013.01);
(Continued)

(58) Field of Classification Search
CPC ........... C12P 19/24; C12N 1/205; C12N 9/90; C12N 15/52; C12N 15/75; C12N 2500/02;
(Continued)

(56) References Cited

FOREIGN PATENT DOCUMENTS

| CN | 104911120 A | * | 9/2015 | ............... C12N 1/20 |
| CN | 112852795 A | * | 5/2021 | ............. C12N 15/70 |
| CN | 113957064 A | * | 1/2022 | |

OTHER PUBLICATIONS

Zaporozhets, A. O., Redko, O. O., Babak, V. P., Eremenko, V. S., & Mokiychuk, V. M. (2018a). Method of indirect measurement of oxygen concentration in the Air. Naukovyi Visnyk Natsionalnoho Hirnychoho Universytetu, (5), 105-114. (Year: 2018).*

(Continued)

*Primary Examiner* — Soren Harward
*Assistant Examiner* — Naghmeh Nina Moazzami (57) ABSTRACT

The present invention relates to the technical field of microbial fermentation engineering, and specifically to a method for producing psicose 3-epimerase by high-density fermentation. In view of the low expression level of psicose 3-epimerase and other problems existing in the current fermentation, by controlling the feeding rate in the fermentation process, improving the culture temperature in the middle and late stages of fermentation and other measures in the present invention, the OD value during the fermentation with recombinant *Bacillus subtilis* and the total enzyme activity of psicose 3-epimerase in the fermentation broth are significantly increased, the expression of psicose 3-epimerase is markedly improved, and the production cost of allulose is reduced. Therefore, the present invention has a very broad prospect of application in industry.

1 Claim, 3 Drawing Sheets

(52) U.S. Cl.
CPC .......... *C12N 15/75* (2013.01); *C12N 2500/02* (2013.01); *C12N 2500/34* (2013.01); *C12N 2500/74* (2013.01); *C12N 2523/00* (2013.01); *C12R 2001/125* (2021.05); *C12Y 501/03* (2013.01)

(58) Field of Classification Search
CPC ............ C12N 2500/34; C12N 2500/74; C12N 2523/00; C12R 2001/125; C12Y 501/03
See application file for complete search history.

(56) References Cited

OTHER PUBLICATIONS

Wang, K., Tian, Y., Zhou, N., Liu, D., & Zhang, D. (2018). Studies on fermentation optimization, stability and application of prolyl aminopeptidase from bacillus subtilis. Process Biochemistry, 74, 10-20. (Year: 2018).*

Suphantharika, M., Ison, A. P., & Lilly, M. D. (1995). The effect of cycling dissolved oxygen tension on the synthesis of the antibiotic difficidin by bacillus subtilis. Bioprocess Engineering, 12(4), 181-186. (Year: 1995).*

Wang, Z., Chen, T., Ma, X., Shen, Z., & Zhao, X. (2011). Enhancement of riboflavin production with bacillus subtilis by expression and site-directed mutagenesis of ZWF and GND gene from Corynebacterium glutamicum. Bioresource Technology, 102 (4), 3934-3940. (Year: 2011).*

Cui, Q., Qian, B., Sun, X., & Zhang, J. (2020). High Cell Density Cultivation of a Recombinant Bacillus Subtilis for Nattokinase Production. (Year: 2020).*

Benz, G. T. (2008). In Process Development Symposium (pp. 32-34). Clarksville, OH; Chemical Product Engineering. (Year: 2008).*

* cited by examiner

METHOD FOR PRODUCING PSICOSE 3-EPIMERASE BY HIGH-DENSITY FERMENTATION

This application claims priority to Chinese Patent Application No. 202210288790.2, filed on Mar. 22, 2022, which is incorporated by reference for all purposes as if fully set forth herein.

FIELD OF THE INVENTION

The present invention relates to the technical field of microbial fermentation engineering, and specifically to a method for producing psicose 3-epimerase by high-density fermentation.

DESCRIPTION OF THE RELATED ART

D-psicose a rare sugar having 70% of the sweetness of sucrose, but low calorie, thus being a good substitute for sucrose. Moreover, D-psicose has a lower absorption rate than that of other sweeteners, can reduce the absorption of fructose and glucose in the body and lower the fat accumulation, thereby reducing the risk of diseases such as type 2 diabetes and obesity. At present, studies have found that D-psicose also has the function of lowering blood lipids and blood glucose. The Food and Drug Administration (FDA) has certified D-psicose as generally recognized as safe (GRAS), so it can be used as a component in food additives. D-psicose has broad prospects of application in food, and health care products.

D-psicose 3-epimerase can epimerize D-fructose into D-psicose, and is a key enzyme in the production of psicose. The production of this enzyme has a great impact on the production cost of psicose.

At present, the research on D-psicose is mainly focused on the construction of engineered recombinant strains, site-directed mutagenesis and directed evolution of the enzyme and immobilization of the enzyme. There are few studies on how to increase the fermentation density of psicose 3-epimerase expressing engineered recombinant strain and significantly increase the expression level.

High-density fermentation refers to a high-efficiency fermentation technology where the cell density is made 10 times higher than that in a conventional technology by controlling the fermentation parameters and feed control in submerged liquid fermentation with the microorganisms. High-density fermentation can increase the cell density in the fermentation tank, and increase the expression of the product, so that the volume of the fermentation tank is correspondingly reduced, the production capacity of the equipment per unit volume is increased, the cost of biomass separation is reduced, and the production period is shortened, thus reducing the production cost, and improving the production efficiency. Therefore, high-density fermentation has great significance in application in industry.

Patent No. CN112852795A provides a method for producing psicose 3-epimerase by fermentation. In the patent, by optimizing the SR medium and the fermentation conditions, the activity of psicose 3-epimerase finally reaches 1436 U/mL. However, a feed control strategy is not adopted during fermentation to achieve high-density fermentation in this method, and the expression level in fermentation still needs to be improved.

SUMMARY OF THE INVENTION

In view of the low expression level of psicose 3-epimerase, low purity, high cost and other defects and shortcomings in the fermentation and production in the prior art, an object of the present invention is to provide a method for producing psicose 3-epimerase by high-density fermentation. The method greatly improves the cell density during fermentation, increases the expression level and purity of psicose 3-epimerase, and reduces the production cost, thus having great significance in application in industry.

The object of the present invention is achieved through the following technical solutions:

A method for producing psicose 3-epimerase by high-density fermentation includes the following steps:

(1) strain activation inoculating a recombinant *Bacillus subtilis* strain into an activation medium and activating, to obtain an activated seed cell suspension; and (2) fermentation culture fermentation culture: adding 1-10% by volume of the activated seed cell suspension cultured in Step (1) to a fermentation medium and fermenting. Initial setting of the fermentation conditions: temperature 37.0° C., air flow rate 1-6 L/min, oxygen flow rate 0-3 L/min, and rotation speed 200-1000 rpm. Control of fermentation process: during the fermentation process, the dissolved oxygen is controlled in a range between 10% and 20%; when $OD_{600}$ rises to 80-120, the fermentation temperature is raised to 40-42° C.; during the fermentation process, when $OD_{600}$ rises to 5-20, a feed medium is fluidically added, at a flow rate of 10-30 mL/h; when $OD_{600}$ rises to 30-50, the feed medium is fluidically added at a flow rate of 30-60 mL/h; when $OD_{600}$ rises to 50-80, the feed medium is fluidically added at a flow rate of 60-90 mL/h; and when $OD_{600}$ rises to 80-100, the feed medium is fluidically added at a flow rate of 90-120 mL/h.

The recombinant *Bacillus subtilis* described in Step (1) is preferably engineered recombinant *Bacillus subtilis* strain B-3-1 (disclosed in Application No. "202010496928.9", entitled "Psicose 3-epimerase mutant, engineered strain expressing the mutant, and use thereof").

The activation medium in Step (1) comprises: peptone 5-15 g/L, yeast powder 1-5 g/L, sodium chloride 8-12 g/L, and kanamycin 25-50 mg/L.

The activation medium in Step (1) preferably comprises: peptone 10 g/L, yeast powder 5 g/L, sodium chloride 10 g/L, kanamycin 25-50 mg/L.

The activation of the recombinant *Bacillus subtilis* in Step (1) preferably comprises specifically:

primary strain activation: inoculating 0.1-1% by volume of frozen recombinant *Bacillus subtilis* cell suspension into the activation medium, and incubating with shaking at a constant temperature, to obtain a primarily activated seed cell suspension, where the incubation temperature is 37.0° C., the rotation speed is 180-220 rpm, and the incubation time is 18-24 h; and secondary strain activation: inoculating 1-10% by volume of the incubated primarily activated seed cell suspension into an activation medium, incubating with shaking at a constant temperature, to obtain a secondarily activated seed cell suspension, where the incubation temperature is 37.0° C., the rotation speed is 180-220 rpm, and the incubation time is 6-12 h.

The primarily activated seed cell suspension is preferably prepared by:

inoculating 0.2% by volume of frozen recombinant *Bacillus subtilis* cell suspension into the activation medium, and incubating with shaking at a constant temperature until the $OD_{600}$ value of the cell culture is 1.0-3.0, to obtain a primarily activated seed cell suspension, where the incubation temperature is 37.0° C., the rotation speed is 200 rpm, and the incubation time is 18-24 h.

The secondarily activated seed cell suspension is preferably prepared by:

inoculating 10% by volume of the incubated primarily activated seed cell suspension into an activation medium, incubating with shaking at a constant temperature until the $OD_{600}$ value of the cell culture is 4.0-6.0, to obtain a secondarily activated seed cell suspension, where the incubation temperature is 37.0° C., the rotation speed is 200 rpm, and the incubation time is 6-12 h.

The fermentation medium in Step (2) comprises: peptone 5-15 g/L, yeast powder 1-5 g/L, potassium dihydrogen phosphate 0.5-5 g/L, dipotassium hydrogen phosphate 5-20 g/L, manganese chloride tetrahydrate 0.02-0.2 g/L, and glucose 2-10 g/L.

The fermentation medium in Step (2) preferably comprises: peptone 10 g/L, and yeast powder 5 g/L, potassium dihydrogen phosphate 2.5 g/L, dipotassium hydrogen phosphate 15 g/L, manganese chloride tetrahydrate 0.1 g/L, and glucose 6 g/L.

The feed medium in Step (2) preferably comprises: 10-30% of glucose and 10-30% of yeast powder based on weight. The specific concentration of the glucose and yeast powder, the feed rate and the feed amount depend on the growth of the strain.

The activation medium, fermentation medium and feed medium in Steps (1) and (2) are preferably sterilized at high temperature. Other components in the activation medium than kanamycin are sterilized at high temperature and then kanamycin is added.

The high-temperature sterilization is preferably sterilization at 121° C. for 20 min.

The fermentation culture in Step (2) preferably comprises:

fermentation culture: adding 10% by volume of the activated seed cell suspension cultured in Step (1) to a fermentation medium and fermenting.

Initial setting of the fermentation conditions is: temperature 37.0° C., air flow rate 5 L/min, oxygen flow rate 1 L/min, and rotation speed 800 rpm. For control of fermentation process: the dissolved oxygen is controlled to 15% during fermentation; when $OD_{600}$ rises to 100, the fermentation temperature is raised to 40° C.; in the fermentation process, when $OD_{600}$ rises to 10, a feed medium is fluidically added at a flow rate of 15 mL/h; when $OD_{600}$ rises to 35, the feed medium is fluidically added at a flow rate of 40 mL/h; when $OD_{600}$ rises to 60, the feed medium is fluidically added at a flow rate of 80 mL/h; and when $OD_{600}$ rises to 90, the feed medium is fluidically added at a flow rate of 110 mL/h.

The method for producing psicose 3-epimerase by high-density fermentation further comprises:

stopping fermentation when the enzyme activity does not increase any longer, obtaining a crude enzyme solution after solid-liquid separation, and obtaining psicose 3-epimerase after further purification.

The method for solid-liquid separation is preferably centrifugation.

The invention also provides use of the method for producing psicose 3-epimerase by high-density fermentation in the production of D-psicose is further provided.

PRINCIPLE OF THE PRESENT INVENTION (1) Inorganic nitrogen (such as ammonium chloride, and ammonium sulfate, etc.) or organic nitrogen (such as peptone, and yeast powder, etc.) can be used in the growth and metabolism of microorganisms. The utilization of inorganic nitrogen requires the microorganisms to convert inorganic nitrogen into amino acids relying on their own metabolism, and then complete the protein expression. This increases the metabolic burden of the cells, affecting the protein expression. In addition, excessive ammonia concentration will also cause ammonia poisoning of the cells. The present invention provides a fermentation medium and feed medium added with organic nitrogen. The amino acids contained can be directly absorbed and utilized by cells, to reduce the metabolic burden of the cells, and to increase the expression of psicose 3-epimerase.

(2) The presence of metal ions is often important for enzyme activity in the following aspects: The metal ions, as a cofactor, form a complex with the enzyme, to become a component in the active center of the enzyme; stabilize the conformation of the enzyme molecules; and can act as a bridge between the enzyme and the substrate. It is found in research that manganese ions promote the enzyme activity of psicose 3-epimerase expressed in the present invention, and the presence of other metal ions such as magnesium ions, calcium ions, iron ions, copper ions, and zinc ions has an inhibitory effect on the enzyme activity. Therefore, an appropriate amount of manganese chloride is added in the fermentation medium of the present invention, to improve the enzyme activity of psicose 3-epimerase.

(3) The enzyme is generally secreted through the transport protein on the cell membrane, and the rate of secretion is limited by the permeability of the cell membrane and the rate of cell metabolism. Moreover, cell death and lysis promote the release of intracellular enzymes, and also the release of intracellular impurity proteins, thus reducing the purity of the target protein, and increasing the difficulty and cost of subsequent separation and purification. In the present invention, a method of raising the culture temperature in the middle and late stages of fermentation is adopted, to improve the permeability of the cell membrane and increase the metabolic rate of the cell, thereby accelerating the secretion of the target enzyme, avoiding the decrease in enzyme purity caused by cell death and lysis in the later stage of fermentation, and facilitating the subsequent separation and purification and cost saving.

(4) During the feed process in the fermentation, the cell density will increase upon feed. A high cell density facilitates the improvement of the enzyme expression. However, if the concentration of glucose in the medium is too high due to improper feed control, CcpA protein (carbon catabolite repression regulator) is induced to express in the cells, thereby inhibiting the transcription and translation of proteins. Moreover, plasmid loss may also be caused by a too high growth rate of the cells due to the high concentration of the carbon source. Therefore, depending on the fact that the amount of nutrients required varies with different cell density at different times, a strategy to adjust the feed rate according to different $OD_{600}$ values is established in the present invention, to maintain the carbon and nitrogen sources at a relatively balanced and low level in the fermentation process, which increases the expression of psicose 3-epimerase, and reduces the production cost of psicose.

The present invention has the following advantages and effects over the prior art.

(1) In the present invention, the organic nitrogen content in the fermentation medium and feed medium is controlled during the fermentation process, to reduce the metabolic burden of the cells, and improve the expression of psicose 3-epimerase.

(2) In the present invention, the content of manganese chloride in the fermentation medium is controlled during the fermentation process, to improve the enzyme activity of psicose 3-epimerase.

(3) In the present invention, a high-density fermentation strategy is adopted and the feed rate at different cell densities is controlled during the fermentation process, to significantly increase the cell density of recombinant *Bacillus subtilis* during fermentation, and increase the $OD_{600}$ value to 150 or higher.

(4) In the present invention, the culture temperature in the middle and late stages of fermentation is increased to 40-42° C., to improve the permeability of the cell membrane and increase the metabolic rate of the cell, thereby accelerating the secretion of the target enzyme, avoiding the decrease in enzyme purity caused by cell death and lysis in the later stage of fermentation, and facilitating the subsequent separation and purification and cost saving.

(5) By the method for producing psicose 3-epimerase provided in the present invention, the total enzyme activity of psicose 3-epimerase in the fermentation broth can be increased to 4783 U/mL. This method significantly improves the expression of psicose 3-epimerase during the fermentation.

(6) The production cost of psicose is reduced in the present invention. Therefore, the present invention has a very broad prospect of application in industry.

DETAILED DESCRIPTION OF THE PREFERRED EMBODIMENTS

The present invention will be further described in detail below with reference to examples and accompanying drawings. However, the present invention is not limited thereto.

The recombinant *Bacillus subtilis* in Step (1) in the examples is engineered recombinant *Bacillus subtilis* strain B-3-1, disclosed the Chinese Patent Application No.: "202010496928.9 entitled "Psicose 3-epimerase mutant, engineered strain expressing the mutant, and use thereof.

The reagents used in examples below are commercially available, unless otherwise specified.

Example 1: High-Density Fermentation (Peptone and Yeast Powder are Used as the Nitrogen Source in the Fermentation Medium and Feed Medium)

(1) Preparation of culture media

A. Activation medium: Composition of activation medium: peptone 10 g/L, yeast powder 5 g/L, and sodium chloride 10 g/L, sterilized at 121° C. for 20 min; and kanamycin 50 mg/L added after sterilization.

B. Fermentation medium: Composition of fermentation medium: peptone 10 g/L, yeast powder 5 g/L, potassium dihydrogen phosphate 2.5 g/L, dipotassium hydrogen phosphate 15 g/L, manganese chloride tetrahydrate 0.1 g/L, and glucose 6 g/L, sterilized at 121° C. for 20 min.

C. Feed medium: Composition of feed medium: 15 wt % of glucose and 20 wt % of yeast powder, sterilized at 121° C. for 20 min.

(2) Strain activation

Primary strain activation: 100 µL of stored cell suspension of engineered recombinant *Bacillus subtilis* strain B-3-1 was inoculated into a 250 mL Erlenmeyer flask containing 50 mL activation medium, and incubated with shaking at a constant temperature until the $OD_{600}$ value of the cell suspension was 2.0, to obtain a primarily activated seed cell suspension. The incubation temperature was 37.0° C., the rotation speed was 200 rpm, and the incubation time was 24 h.

Secondary strain activation: 50 mL of the primarily activated seed cell suspension incubated was inoculated into a 3000 mL Erlenmeyer flask containing 500 mL activation medium, and incubated with shaking at a constant temperature until the $OD_{600}$ value of the cell suspension was 5.0, to obtain a secondarily activated seed cell suspension. The incubation temperature was 37.0° C., the rotation speed was 200 rpm, and the incubation time was 8 h.

(3) Fermentation culture fermentation culture: 3150 mL of a fermentation medium was added to a 5 L fermentation tank, and sterilized at 121° C. for 20 min. 350 mL of the secondarily activated seed cell suspension obtained in Step (2) was added to the fermentation medium, and fermented. Initial setting of the fermentation conditions: temperature 37.0° C., air flow rate 5 L/min, oxygen flow rate 1 L/min, and rotation speed 800 rpm. Control of fermentation process: during the fermentation process, the dissolved oxygen was controlled to 15%; when $OD_{600}$ rose to 100, the fermentation temperature was raised to 40° C.; during the fermentation process, when $OD_{600}$ rose to 10, a feed medium was fluidically added at a flow rate of 15 mL/h; when $OD_{600}$ rose to 35, the feed medium was fluidically added at a flow rate of 40 mL/h; when $OD_{600}$ rose to 60, the feed medium was fluidically added at a flow rate of 80 mL/h; and when $OD_{600}$ rose to 90, the feed medium was fluidically added at a flow rate of 110 mL/h.

(4) Discharge from fermentation tank: The fermentation was stopped when the enzyme activity did not increase any longer, and the fermentation broth was centrifuged at 4000 rpm for 30 min, to obtain a crude enzyme solution.

Example 2: High-Density Fermentation (Peptone and Yeast Powder are Used as the Nitrogen Source in the Fermentation Medium and Feed Medium)

(1) Preparation of culture media

A. Activation medium: Composition of activation medium: peptone 5 g/L, yeast powder 1 g/L, and sodium chloride 8 g/L, sterilized at 121° C. for 20 min; and kanamycin 25 mg/L added after sterilization.

B. Fermentation medium: Composition of fermentation medium: peptone 5 g/L, yeast powder 1 g/L, potassium dihydrogen phosphate 0.5 g/L, dipotassium hydrogen phosphate 5 g/L, manganese chloride tetrahydrate 0.02 g/L, and glucose 2 g/L, sterilized at 121° C. for 20 min.

C. Feed medium: Composition of feed medium: 10 wt % of glucose and 10 wt % of yeast powder, sterilized at 121° C. for 20 min.

(2) Strain activation

Primary strain activation: 50 μL of stored cell suspension of engineered recombinant *Bacillus subtilis* strain B-3-1 was inoculated into a 250 mL Erlenmeyer flask containing 50 mL activation medium, and incubated with shaking at a constant temperature until the $OD_{600}$ value of the cell suspension was 1.0, to obtain a primarily activated seed cell suspension. The incubation temperature was 37.0° C., the rotation speed was 180 rpm, and the incubation time was 24 h.

Secondary strain activation: 5 mL of the primarily activated seed cell suspension incubated was inoculated into a 3000 mL Erlenmeyer flask containing 500 mL activation medium, and incubated with shaking at a constant temperature until the $OD_{600}$ value of the cell suspension was 4.0, to obtain a secondarily activated seed cell suspension. The incubation temperature was 37.0° C., the rotation speed was 180 rpm, and the incubation time was 12 h.

(3) Fermentation culture fermentation culture: 3150 mL of a fermentation medium was added to a 5 L fermentation tank, and sterilized at 121° C. for 20 min. 350 mL of the secondarily activated seed cell suspension obtained in Step (2) was added to the fermentation medium, and fermented. Initial setting of the fermentation conditions: temperature 37.0° C., air flow rate 1 L/min, oxygen flow rate 0 L/min, and rotation speed 200 rpm. Control of fermentation process: during the fermentation process, the dissolved oxygen was controlled to 10%; when $OD_{600}$ rose to 80, the fermentation temperature was raised to 40° C.; during the fermentation process, when $OD_{600}$ rose to 5, a feed medium was fluidically added at a flow rate of 10 mL/h; when $OD_{600}$ rose to 30, the feed medium was fluidically added at a flow rate of 30 mL/h; when $OD_{600}$ rose to 50, the feed medium was fluidically added at a flow rate of 60 mL/h; and when $OD_{600}$ rose to 80, the feed medium was fluidically added at a flow rate of 90 mL/h.

(4) Discharge from fermentation tank: The fermentation was stopped when the enzyme activity did not increase any longer, and the fermentation broth was centrifuged at 4000 rpm for 30 min, to obtain a crude enzyme solution.

Example 3: High-Density Fermentation (Peptone and Yeast Powder are Used as the Nitrogen Source in the Fermentation Medium and Feed Medium)

(1) Preparation of culture media

A. Activation medium: Composition of activation medium: peptone 15 g/L, yeast powder 5 g/L, and sodium chloride 10 g/L, sterilized at 121° C. for 20 min; and kanamycin 50 mg/L added after sterilization.

B. Fermentation medium: Composition of fermentation medium: peptone 15 g/L, yeast powder 5 g/L, potassium dihydrogen phosphate 5 g/L, dipotassium hydrogen phosphate 20 g/L, manganese chloride tetrahydrate 0.2 g/L, and glucose 10 g/L, sterilized at 121° C. for 20 min.

C. Feed medium: Composition of feed medium: 30 wt % of glucose and 30 wt % of yeast powder, sterilized at 121° C. for 20 min.

(2) Strain activation

Primary strain activation: 500 μL of stored cell suspension of engineered recombinant *Bacillus subtilis* strain B-3-1 was inoculated into a 250 mL Erlenmeyer flask containing 50 mL activation medium, and incubated with shaking at a constant temperature until the $OD_{600}$ value of the cell suspension was 3.0, to obtain a primarily activated seed cell suspension. The incubation temperature was 37.0° C., the rotation speed was 220 rpm, and the incubation time was 18 h.

Secondary strain activation: 50 mL of the primarily activated seed cell suspension incubated was inoculated into a 3000 mL Erlenmeyer flask containing 500 mL activation medium, and incubated with shaking at a constant temperature until the $OD_{600}$ value of the cell suspension was 6.0, to obtain a secondarily activated seed cell suspension. The incubation temperature was 37.0° C., the rotation speed was 220 rpm, and the incubation time was 6 h.

(3) Fermentation culture fermentation culture: 3150 mL of a fermentation medium was added to a 5 L fermentation tank, and sterilized at 121° C. for 20 min. 350 mL of the secondarily activated seed cell suspension obtained in Step (2) was added to the fermentation medium, and fermented. Initial setting of the fermentation conditions: temperature 37.0° C., air flow rate 6 L/min, oxygen flow rate 3 L/min, and rotation speed 1000 rpm. Control of fermentation process: during the fermentation process, the dissolved oxygen was controlled to 20%; when $OD_{600}$ rose to 120, the fermentation temperature was raised to 42° C.; during the fermentation process, when $OD_{600}$ rose to 20, a feed medium was fluidically added at a flow rate of 30 mL/h; when $OD_{600}$ rose to 50, the feed medium was fluidically added at a flow rate of 60 mL/h; when $OD_{600}$ rose to 80, the feed medium was fluidically added at a flow rate of 90 mL/h; and when $OD_{600}$ rose to 100, the feed medium was fluidically added at a flow rate of 120 mL/h.

(4) Discharge from fermentation tank: The fermentation was stopped when the enzyme activity did not increase any longer, and the fermentation broth was centrifuged at 4000 rpm for 30 min, to obtain a crude enzyme solution.

Comparative Example 1: Constant-Temperature Fermentation at 37° C. Without Feed (1) Preparation of media:

A. Activation medium: The same as that in Example 1.

B. Fermentation medium: The same as that in Example 1.

(2) Strain activation

Primary strain activation: The same as that in Example 1.

Secondary strain activation: The same as that in Example 1.

(3) Fermentation culture fermentation culture: 3150 mL of the fermentation medium was added to a 5 L fermentation tank, and sterilized at 121° C. for 20 min. 350 mL of the secondarily activated seed cell suspension obtained in Step (2) was added to the fermentation medium, and fermented. Initial setting of the fermentation conditions: temperature 37.0° C., air flow rate 5 L/min, oxygen flow rate 1 L/min, and rotation speed 800 rpm. Control of fermentation process: During the fermentation process, the dissolved oxygen was controlled to 15% by controlling the rotation speed and the rate of introducing pure oxygen.

(4) Discharge from fermentation tank: The same as that in Example 1.

(5)

Comparative Example 2: Constant-Temperature Fermentation at 37° C. with Feed (1) Preparation of media:
A. Activation medium: The same as that in Example 1.
B. Fermentation medium: The same as that in Example 1.
C. Feed medium: The same as that in Example 1.
(2) Strain activation
Primary strain activation: The same as that in Example 1.
Secondary strain activation: The same as that in Example 1.
(3) Fermentation culture: 3150 mL of the fermentation medium was added to a 5 L fermentation tank, and sterilized at 121° C. for 20 min. 350 mL of the secondarily activated seed cell suspension obtained in Step (2) was added to the fermentation medium, and fermented. Initial setting of the fermentation conditions: temperature 37.0° C., air flow rate 5 L/min, oxygen flow rate 1 L/min, and rotation speed 800 rpm. Control of fermentation process: during the fermentation process, the dissolved oxygen was controlled to 15%; during the fermentation process, when $OD_{600}$ rose to 10, a feed medium was fluidically added at a flow rate of 15 mL/h. when $OD_{600}$ rose to 35, the feed medium was fluidically added at a flow rate of 40 mL/h; when $OD_{600}$ rose to 60, the feed medium was fluidically added at a flow rate of 80 mL/h; and when $OD_{600}$ rose to 90, the feed medium was fluidically added at a flow rate of 110 mL/h.
(4) Discharge from fermentation tank: The same as that in Example 1.

Comparative Example 3: Fermentation without Feed where the Temperature is Increased to 40° C. in the Middle and Late Stages of Fermentation (1) Preparation of media:
A. Activation medium: The same as that in Example 1.
B. Fermentation medium: The same as that in Example 1.
(2) Strain activation
Primary strain activation: The same as that in Example 1.
Secondary strain activation: The same as that in Example 1.
(3) Fermentation culture
fermentation culture: 3150 mL of the fermentation medium was added to a 5 L fermentation tank, and sterilized at 121° C. for 20 min. 350 mL of the secondarily activated seed cell suspension obtained in Step (2) was added to the fermentation medium, and fermented. Initial setting of the fermentation conditions: temperature 37.0° C., air flow rate 5 L/min, oxygen flow rate 1 L/min, and rotation speed 800 rpm. Control of fermentation process: During the fermentation process, the dissolved oxygen was controlled to 15% by controlling the rotation speed and the rate of introducing pure oxygen. When $OD_{600}$ rose to 20, the fermentation temperature was raised to 40° C.
(4) Discharge from fermentation tank: The same as that in Example 1.

Comparative Example 4: Fermentation with Fermentation Medium and Feed Medium Using Ammonia Chloride as Nitrogen Source (1) Preparation of media:
A. Activation medium: The same as that in Example 1.
B. Fermentation medium: Composition of fermentation medium: ammonia chloride 5 g/L, potassium dihydrogen phosphate 2.5 g/L, dipotassium hydrogen phosphate 15 g/L, manganese chloride tetrahydrate 0.1 g/L, and glucose 6 g/L, sterilized at 121° C. for 20 min.
C. Feed medium: Composition of feed medium: 20 wt % of glucose and 10 wt % of ammonia chloride sterilized at 121° C. for 20 min.
(2) Strain activation
Primary strain activation: The same as that in Example 1.
Secondary strain activation: The same as that in Example 1.
(3) Fermentation culture
fermentation culture: 3150 mL of the fermentation medium was added to a 5 L fermentation tank, and sterilized at 121° C. for 20 min. 350 mL of the secondarily activated seed cell suspension obtained in Step (2) was added to the fermentation medium, and fermented. Initial setting of the fermentation conditions: temperature 37.0° C., air flow rate 5 L/min, oxygen flow rate 1 L/min, and rotation speed 800 rpm. Control of fermentation process: during the fermentation process, the dissolved oxygen was controlled to 15%; when $OD_{600}$ rose to 100, the fermentation temperature was raised to 40° C.; during the fermentation process, when $OD_{600}$ rose to 10, a feed medium was fluidically added at a flow rate of 15 mL/h. when $OD_{600}$ rose to 35, the feed medium was fluidically added at a flow rate of 40 mL/h; when $OD_{600}$ rose to 60, the feed medium was fluidically added at a flow rate of 80 mL/h; and when $OD_{600}$ rose to 90, the feed medium was fluidically added at a flow rate of 110 mL/h.
(4) Discharge from fermentation tank: The same as that in Example 1.

Effect Examples (1) Sample Detection During Fermentation
① Absorbance detection: In Example 1 and Comparative Examples 1-4, the fermentation broth was sampled every 4 h after the start of fermentation, and the $OD_{600}$ value of the fermentation broth was detected by an ultraviolet spectrophotometer and recorded. A growth curve was plotted.
② Enzyme activity detection: A 10 wt % fructose solution (potassium phosphate buffer pH 8.0, containing 1 mM $Mn^{2+}$) was used as a substrate, and an appropriate amount of the fermentation broth from Comparative Examples 1~4 was added and reacted at 60° C. for 20 min. After the reaction, the reaction system was treated in a boiling water bath for 5 min, and the content of the product D-psicose was determined by HPLC, from which the enzyme activity was calculated.

(2) Detection by SDS-PAGE:

The crude enzyme solutions prepared in Example 1, Comparative Example 1 and Comparative Example 4 were diluted to have the same enzyme activity (100 U/mL), and a loading buffer was added, mixed uniformly, and boiled at 100° C. for 10 min. The sample was loaded in a volume of 10 μL, and subjected to electrophoresis, under conditions including: extraction gel of 12%, concentration gel of 5%, and constant voltage of 100 V.

TABLE 1

Comparison and analysis of results of fermentation in Example 1 and Comparative Examples 1-4

|  | Example 1 | Comparative Example 1 | Comparative Example 2 | Comparative Example 3 | Comparative Example 4 |
|---|---|---|---|---|---|
| $OD_{600\ value}$ in lower tank | 158 | 21 | 146 | 34 | 110 |
| Enzyme activity U/mL | 4783 | 1584 | 3272 | 1501 | 2002 |

Figure 6:
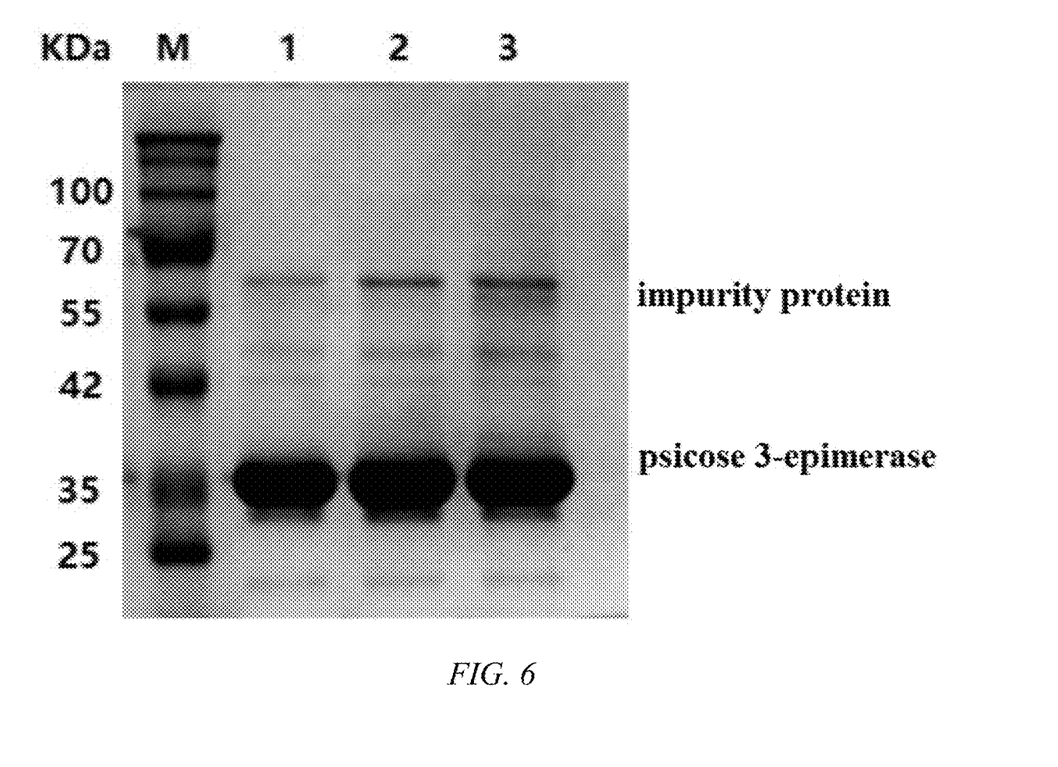
FIG. 6 shows an electrophoretogram of a crude enzyme solution at the end of fermentation in Example 1, Comparative Example 1 and Comparative Example 4 (where the sample is diluted to have the same enzyme activity, and the volume of the sample is the same), wherein, 1: Sample of Example 1, 2: Sample of Comparative Example 1, 3: Sample of Comparative Example 4, M: Maker.

The present inventor finds surprisingly that the rate of enzyme secretion by the engineered recombinant *Bacillus subtilis* strain B-3-1 is limited during the fermentation culture process. In Comparative Example 1, high enzyme activity can also be detected in the cells in the middle and late stages of fermentation, indicating that some enzymes have not been secreted to the outside of the cells. After further culture for a period of time, the cell density decreases. At this time, the enzyme activity reaches its highest (Table 1, and FIG. 3), suggesting that the cells are lysed to releases the enzyme in the cells. However, the lysis of the cells also releases the impurity proteins in the cells, resulting in more impurity proteins in the crude enzyme solution, and causing increased difficulty and cost of purification (FIG. 6).

Figure 3:
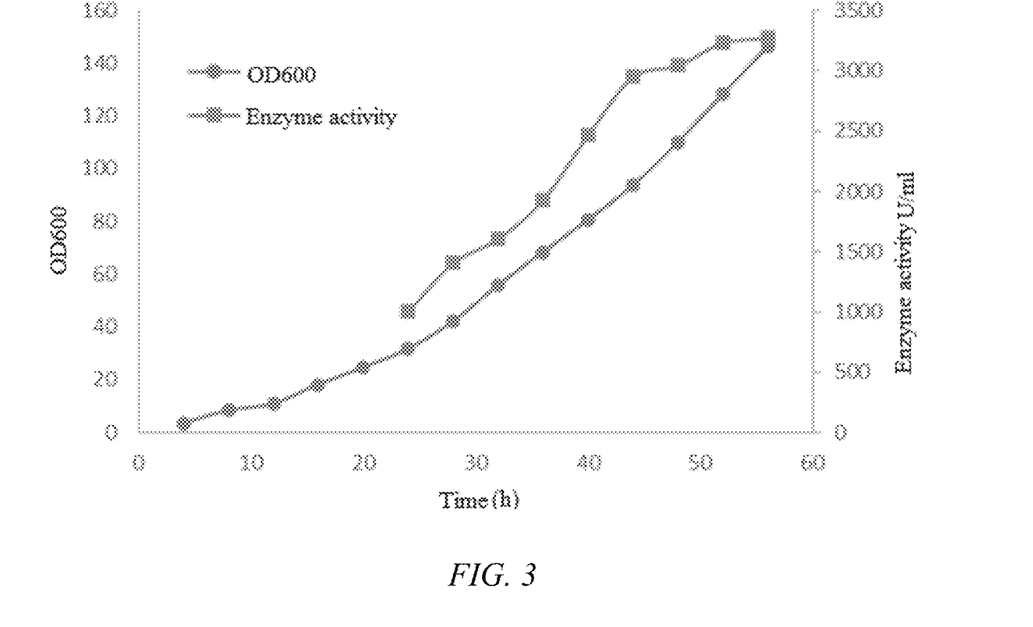
FIG. 3 shows a growth curve of recombinant *Bacillus subtilis* and an enzyme activity curve determined in the fermentation process in Comparative Example 2.

Comparative Example 2 differs from Example 1 by constant-temperature fermentation at 37° C. and differs from Comparative Example 1 by feed fermentation. As can be seen from FIG. 3, compared with Comparative Example 1, feed fermentation in Comparative Example 2 can improve the cell density and enzyme activity in the fermentation tank; however, the enzyme activity in Example 1 is significantly higher than that in Comparative Example 2, indicating that the increase of the culture temperature in the middle and late stages of fermentation to an appropriate temperature can accelerate the secretion of the target enzyme.

Figure 4:
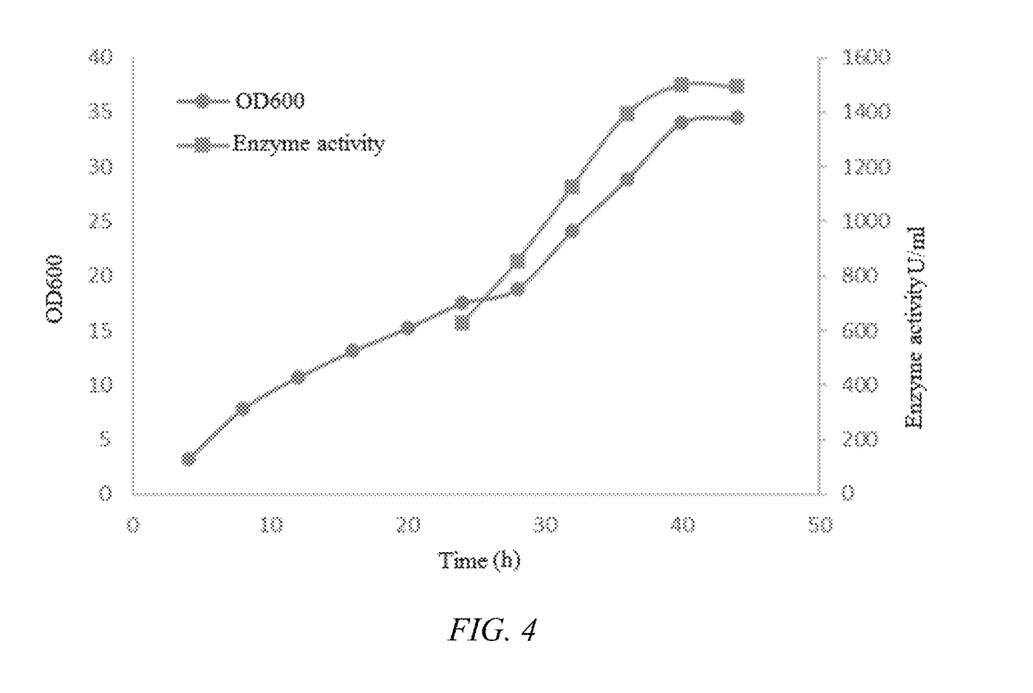
FIG. 4 shows a growth curve of recombinant *Bacillus subtilis* and an enzyme activity curve determined in the fermentation process in Comparative Example 3.

Comparative Example 3 differs from Example 1 by fermentation without feed where the temperature is increased to 40° C. in the middle and late stages of fermentation. As can be seen from FIG. 4, the measure of increasing the culture temperature in the middle and late stages of fermentation used alone cannot effectively improve the cell density and enzyme activity. However, compared with Comparative Example 1, the fermentation period can be shortened from 48 h to 40 h, while the enzyme activity during fermentation is not much different from that in Comparative Example 1. It further indicates that increasing the temperature in the late stage of fermentation can accelerate the secretion rate of the enzyme.

Figure 5:
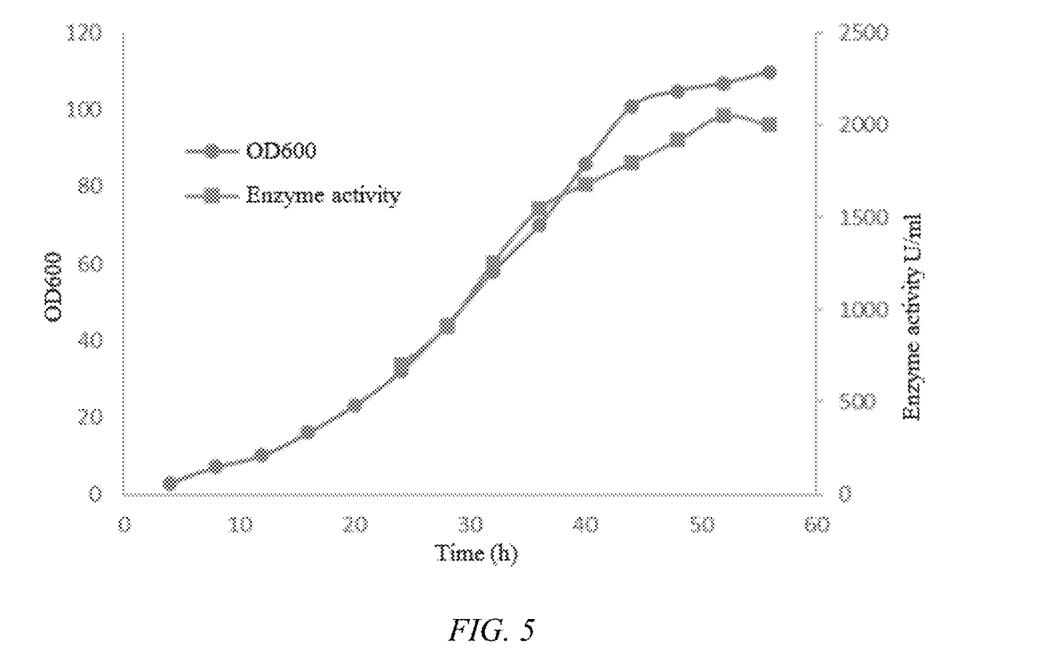
FIG. 5 shows a growth curve of recombinant *Bacillus subtilis* and an enzyme activity curve determined in the fermentation process in Comparative Example 4.

Comparative Example 4 differs from Example 1 by using the inorganic nitrogen source ammonium chloride in the fermentation medium and feed medium. As can be seen from FIG. 5, the use of the inorganic nitrogen source reduces the cell density, and causes the enzyme activity to decrease by at least one time. The organic nitrogen source used in Example 1 reduces the metabolic burden of the cells, and increases the cell density and the expression of psicose 3-epimerase. Organic nitrogen (such as peptone, and yeast powder, etc.) is preferred to be used in the growth and metabolism of microorganisms. The utilization of inorganic nitrogen requires the microorganisms to convert inorganic nitrogen into amino acids relying on their own metabolism, and then complete the protein expression. This increases the metabolic burden of the cells, affecting the protein expression. It can be seen from FIGS. 1 and 5 that although high-density fermentation is used in both Example 1 and Comparative Example 4, the protein expression is more than 1 times different. This can be attributed to the type of nitrogen source used in the fermentation process. The inorganic nitrogen is more conducive to the cell growth, and the organic nitrogen is more conducive to the protein expression.

Figure 1:
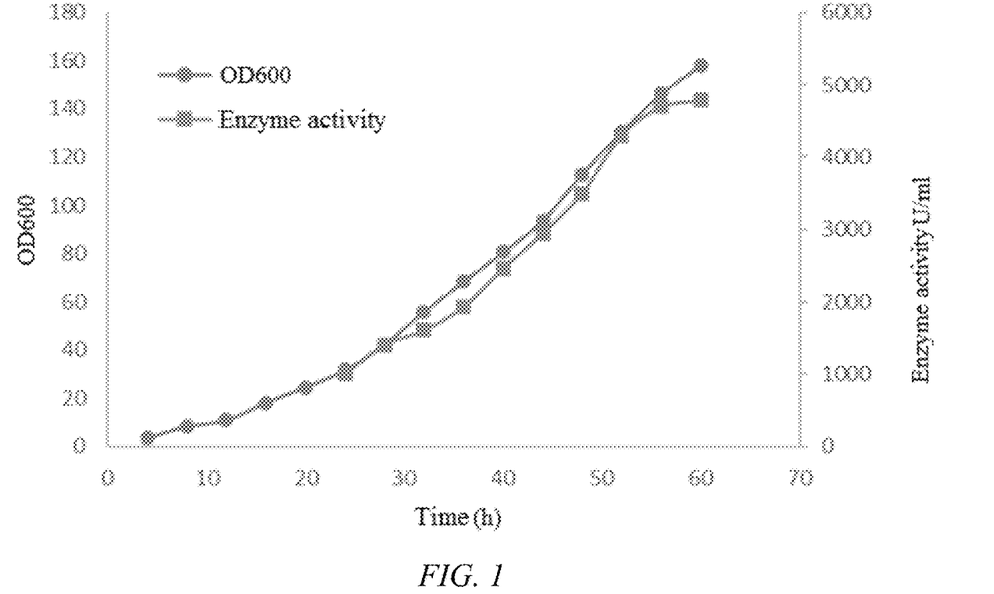
FIG. 1 shows a growth curve of recombinant *Bacillus subtilis* and an enzyme activity curve determined in the fermentation process in Example 1.
Figure 2:
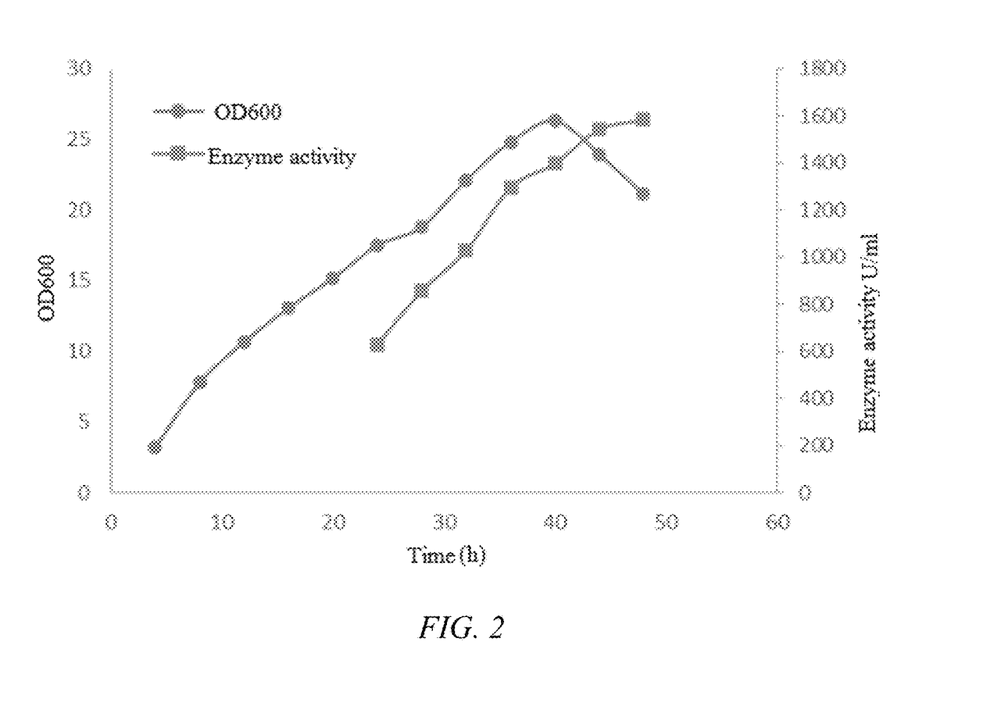
FIG. 2 shows a growth curve of recombinant *Bacillus subtilis* and an enzyme activity curve determined in the fermentation process in Comparative Example 1.

It can be seen from FIGS. 1 and 6 that by feed control during fermentation in Example 1, the cell density is kept to rise continuously; by Increasing the culture temperature in the late stage of fermentation, the permeability of the cell membrane is improved and the rate of enzyme secretion is significantly increased. There is no need for the lysis of cells to release the intracellular enzymes and impurity proteins, the fermentation period is shortened and the purity of the crude enzyme solution is improved accordingly. Using the method in Example 1, the cell density upon discharge from the tank is increased by nearly 6 times, and the enzyme activity is increased by about 2 times.

Preferred embodiments of the present invention have been described above; however, the present invention is not limited thereto. Any other changes, modifications, alternatives, combinations, simplifications made without departing from the spirit and principle of the present invention are all equivalent replacements, and embraced in the protection scope of the present invention.

What is claimed is:

1. A method for producing a psicose 3-epimerase by fermentation, consisting of:
    (1) inoculating 0.1-1% by volume of a frozen recombinant *Bacillus subtilis* cell suspension into an activation medium and incubating at 37.0° C. and at a rotation speed is 200 rpm for 18-24 hours to obtain a primarily activated seed cell suspension, the primarily activated seed cell suspension having an $OD_{600}$ value of 1.0-3.0; and inoculating 1-10% by volume of the primarily activated seed cell suspension into the activation medium and incubating at 37.0° C. and at a rotation speed is 200 rpm for 6-12 hours to obtain an activated seed cell suspension, the activated seed cell suspension having an $OD_{600}$ value of 4.0-6.0;
    (2) adding 10% by volume of the activated seed cell suspension cultured to a fermentation medium to obtain a fermentation solution and conducting a fermentation; and
    (3) stopping fermentation, conducting a solid-liquid separation to obtain a crude enzyme solution including psicose 3-epimerase, and conducting a further purification to obtain the psicose 3-epimerase,
    wherein the initial setting of the fermentation consisting of: a fermentation temperature of 37.0° C., an air flow rate of 5 L/min, an oxygen flow rate of 1 L/min, and a rotation speed of 800 rpm;
    wherein a control of the fermentation consisting of: controlling dissolved oxygen to 15% during fermentation, when an $OD_{600}$ value of the fermentation solution rises to 100, raising the fermentation temperature to 40° C.; when the $OD_{600}$ value of the fermentation solution rises to 10, adding a feed medium at a flow rate of 15 mL/h; when the $OD_{600}$ value of the fermentation solution rises to 35, adding the feed medium is at a flow rate of 40 mL/h; when the $OD_{600}$ value of the fermentation solution rises to 60, adding the feed medium at a flow rate of 80 mL/h; and when the $OD_{600}$ value of the fermentation solution rises to 90, adding the feed medium added at a flow rate of 110 mL/h;

wherein the activation medium consisting of: 5-10 g/L peptone, 1-5 g/L yeast powder, 8-12 g/L sodium chloride, 25-50 mg/L kanamycin, and water;

wherein the fermentation medium consisting of: 10 g/L peptone, 5 g/L yeast powder, 2.5 g/L potassium dihydrogen phosphate, 15 g/L dipotassium hydrogen phosphate, 0.1 g/L manganese chloride tetrahydrate, 6 g/L glucose, and water; and wherein the feed medium consisting of: 10-30% glucose, 10-30% of yeast powder by weight, and water.

\* \* \* \* \*